(12) United States Patent
Harr et al.

(10) Patent No.: US 7,980,521 B2
(45) Date of Patent: Jul. 19, 2011

(54) MEDICAL DEVICE SAFETY SUPPORT WITH INFINITE POSITIONING

(75) Inventors: James Harr, Foristell, MO (US); Glenn Fournie, Smithton, IL (US); Joel D. Wiesner, St. Peters, MO (US); Scott Kimsey, Hebron, KY (US); Ricky A. Sisk, Washington, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 1020 days.

(21) Appl. No.: 11/744,710

(22) Filed: May 4, 2007

(65) Prior Publication Data
US 2008/0272254 A1 Nov. 6, 2008

(51) Int. Cl.
*F16B 1/00* (2006.01)
(52) U.S. Cl. ............... 248/229.1; 248/539; 248/220.21; 248/229.14; 248/224.7
(58) Field of Classification Search .......... 248/540, 248/539, 534, 535, 536, 220.21, 229.1, 229.14, 248/224.7; 411/92
See application file for complete search history.

(56) References Cited

U.S. PATENT DOCUMENTS

| | | |
|---|---|---|
| 184,957 A | 12/1876 | Doeg |
| 252,969 A | 1/1882 | Porter |
| 291,248 A | 1/1884 | West |
| 989,893 A | 4/1911 | Brick |
| 1,059,217 A | 4/1913 | Rudy |
| 1,066,357 A | 7/1913 | Yardley |
| 1,160,103 A | 11/1915 | Burkhart |
| 1,403,863 A | 1/1922 | Peat |
| 1,749,491 A | 3/1930 | Kokay |
| 2,101,317 A | 12/1937 | Lemieux |
| 2,116,263 A | 5/1938 | Harbaugh |
| 2,322,107 A | 6/1943 | Balcar |
| 2,448,402 A | 8/1948 | Thompson |
| 2,502,684 A * | 4/1950 | Ward .............. 248/515 |
| 2,516,759 A * | 7/1950 | Diderrich ........ 248/515 |
| 2,638,301 A | 5/1953 | Smith |
| 2,729,126 A * | 1/1956 | Stanton, Jr. et al. ...... 269/137 |
| 2,756,789 A | 7/1956 | Kraus et al. |
| 2,867,003 A | 1/1959 | Stiles |
| 2,945,946 A | 7/1960 | Moffatt |
| 3,268,853 A | 8/1966 | Noker et al. |
| 3,304,036 A * | 2/1967 | Davis .............. 248/514 |
| 3,442,478 A | 5/1969 | Parapetti |
| 3,803,012 A | 4/1974 | Kurr |

(Continued)

FOREIGN PATENT DOCUMENTS
EP 0167345 A1 1/1986

*Primary Examiner* — Anita M King
(74) *Attorney, Agent, or Firm* — Elias Domingo, Esq.

(57) ABSTRACT

A medical device safety support apparatus features a clamp member configured to be attached to an IV pole, a bed rail, or other support structure. A medical device support member extends from the clamp member and is configured to support a cooperatively configured medical device. The medical device support member may include a socket which receives a post that extends from the medical device, and a lockdown member having a set-screw portion and a handle is provided to secure the post within the socket. The post has a circumferential channel in which the set-screw portion seats, thereby allowing the post to be retained within the socket when the lockdown member is loosened so as to prevent the medical device from being removed from the support member.

11 Claims, 10 Drawing Sheets

U.S. PATENT DOCUMENTS

| | | |
|---|---|---|
| 3,883,128 A | 5/1975 | Breese |
| 4,164,344 A | 8/1979 | Deragne |
| 4,262,872 A | 4/1981 | Kodet |
| 4,365,792 A | 12/1982 | Johns |
| 4,432,538 A | 2/1984 | Sequin |
| 4,443,128 A | 4/1984 | Yamamoto et al. |
| 4,464,090 A * | 8/1984 | Duran ........................... 411/103 |
| 4,487,523 A | 12/1984 | Monroe |
| 4,500,077 A | 2/1985 | Coxon |
| 4,504,046 A | 3/1985 | Yonezawa et al. |
| 4,547,092 A | 10/1985 | Vetter et al. |
| 4,560,152 A | 12/1985 | Miller |
| 4,576,501 A | 3/1986 | McConnell |
| 4,676,687 A | 6/1987 | Koffler |
| 4,695,025 A | 9/1987 | Vaughan |
| 4,697,800 A | 10/1987 | Stahl et al. |
| 4,699,344 A | 10/1987 | Vaughan |
| 4,702,448 A | 10/1987 | LoJacono et al. |
| 4,706,368 A | 11/1987 | Crissman, III et al. |
| 4,742,981 A | 5/1988 | Converse |
| 4,796,846 A | 1/1989 | Meier et al. |
| 4,832,294 A | 5/1989 | Eidem |
| 4,832,299 A | 5/1989 | Gorton et al. |
| 4,842,174 A | 6/1989 | Sheppard et al. |
| 4,850,099 A | 7/1989 | Scollard |
| 4,852,841 A | 8/1989 | Sebring |
| 4,865,484 A | 9/1989 | McConnell |
| 4,881,843 A | 11/1989 | Randleman |
| 4,885,667 A | 12/1989 | Selden |
| 4,906,150 A * | 3/1990 | Bennett ........................ 411/119 |
| 4,957,021 A | 9/1990 | Helton |
| 4,958,873 A | 9/1990 | Akagawa |
| 4,969,768 A | 11/1990 | Young |
| 4,982,988 A | 1/1991 | Murphy |
| 5,025,780 A | 6/1991 | Farley |
| 5,039,056 A * | 8/1991 | Paxton ........................... 248/539 |
| 5,108,213 A | 4/1992 | Shields |
| 5,118,127 A | 6/1992 | Partington |
| 5,139,359 A | 8/1992 | Rakar et al. |
| 5,161,787 A | 11/1992 | Hobday |
| 5,163,752 A | 11/1992 | Copeland et al. |
| 5,174,533 A | 12/1992 | Pryor et al. |
| 5,197,360 A | 3/1993 | Wooster, Jr. |
| 5,226,638 A | 7/1993 | Ausilio |
| 5,236,213 A | 8/1993 | Trickett |
| 5,242,240 A | 9/1993 | Gorham |
| 5,246,217 A | 9/1993 | Brot |
| 5,312,094 A | 5/1994 | Zera |
| 5,314,175 A | 5/1994 | Izumi et al. |
| 5,320,444 A | 6/1994 | Bookwalter et al. |
| 5,326,059 A | 7/1994 | Pryor et al. |
| 5,332,184 A | 7/1994 | Davis |
| 5,342,011 A | 8/1994 | Short |
| 5,346,194 A | 9/1994 | Coffin, III |
| 5,383,636 A * | 1/1995 | Karl ........................... 248/229.15 |
| 5,385,324 A | 1/1995 | Pryor et al. |
| 5,415,383 A | 5/1995 | Ausilio |
| 5,431,364 A * | 7/1995 | Etter ........................... 248/514 |
| 5,443,246 A | 8/1995 | Peterson |
| 5,454,551 A | 10/1995 | Hobday |
| 5,476,252 A | 12/1995 | Yonezawa |
| 5,501,435 A | 3/1996 | Monteiro |
| 5,516,088 A | 5/1996 | Coffin, III |
| 5,529,297 A | 6/1996 | Sawdon |
| 5,580,035 A | 12/1996 | Ffield et al. |
| 5,582,379 A | 12/1996 | Keselman et al. |
| 5,586,754 A | 12/1996 | Williams |
| 5,595,375 A | 1/1997 | Bennhausen |
| 5,615,968 A | 4/1997 | Verenski et al. |
| 5,657,972 A | 8/1997 | Blatt |
| 5,664,750 A * | 9/1997 | Cohen ........................ 248/231.71 |
| 5,695,177 A | 12/1997 | Mascola |
| D389,334 S * | 1/1998 | Attridge ........................ D6/418 |
| 5,704,577 A | 1/1998 | Gordon |
| 5,727,899 A | 3/1998 | Dobrovolny |
| 5,733,061 A | 3/1998 | Child |
| 5,746,422 A | 5/1998 | Harada et al. |
| 5,807,333 A | 9/1998 | Osborne et al. |
| 5,820,116 A | 10/1998 | Haese |
| 5,823,657 A * | 10/1998 | Price et al. ..................... 362/191 |
| 5,826,310 A | 10/1998 | Hobday |
| 5,827,026 A | 10/1998 | Patti |
| 5,836,573 A | 11/1998 | Hayashi et al. |
| 5,868,710 A | 2/1999 | Battiato et al. |
| 5,873,386 A | 2/1999 | Arosio |
| 5,892,344 A | 4/1999 | Cooley |
| 5,899,445 A | 5/1999 | Kimble |
| 5,913,509 A | 6/1999 | Price et al. |
| D413,429 S * | 9/1999 | Carson ........................... D3/10 |
| 6,024,350 A | 2/2000 | Price et al. |
| 6,039,313 A | 3/2000 | Baculy |
| 6,073,285 A | 6/2000 | Ambach et al. |
| 6,073,920 A | 6/2000 | Colley |
| 6,079,703 A | 6/2000 | Chavez, Jr. |
| 6,102,383 A | 8/2000 | Tunkers |
| 6,109,602 A | 8/2000 | Schron, Jr. et al. |
| 6,139,000 A | 10/2000 | Price et al. |
| 6,241,231 B1 | 6/2001 | Schron, Jr. et al. |
| 6,326,059 B1 | 12/2001 | Lewin et al. |
| 6,338,478 B2 | 1/2002 | Baculy |
| 6,340,154 B1 | 1/2002 | Young |
| 6,382,576 B1 | 5/2002 | Heimbrock |
| 6,394,437 B1 | 5/2002 | Yonezawa |
| 6,402,130 B1 | 6/2002 | Price et al. |
| 6,402,131 B1 | 6/2002 | Baculy |
| 6,481,204 B1 | 11/2002 | Yuschak et al. |
| D470,400 S * | 2/2003 | Fraser et al. ................... D8/396 |
| 6,520,495 B1 | 2/2003 | La Mendola |
| 6,619,599 B2 | 9/2003 | Elliott et al. |
| 6,634,823 B2 | 10/2003 | Sciortino |
| 6,644,636 B1 | 11/2003 | Ryan |
| 6,690,280 B2 | 2/2004 | Citrenbaum et al. |
| 6,758,467 B2 | 7/2004 | Kitaura |
| 6,942,637 B2 | 9/2005 | Cartledge et al. |
| 6,942,647 B2 | 9/2005 | Nickels |
| 7,395,563 B2 | 7/2008 | Whitmore, III et al. |
| 2003/0019038 A1 | 1/2003 | Welling et al. |
| 2005/0006542 A1 | 1/2005 | Henning et al. |
| 2005/0267449 A1 | 12/2005 | Edoga et al. |
| 2006/0278785 A1 | 12/2006 | Wiesner et al. |
| 2007/0129634 A1 | 6/2007 | Hickey et al. |
| 2007/0220671 A1 | 9/2007 | Vanderheiden et al. |

* cited by examiner

MEDICAL DEVICE SAFETY SUPPORT WITH INFINITE POSITIONING

BACKGROUND AND FIELD OF THE INVENTION

This invention relates to support apparatus for medical devices. More particularly, the invention relates to a support apparatus that permits a supported medical device to be rotated relative to a support structure in an infinite number of positions without removing the medical device from the support apparatus or support structure. The support device also prevents the attached medical device from falling off when loosened.

Medical devices such as enteral feeding pumps are typically attached to a support structure such as an IV pole, a bed rail, or other support structure by means of a pole clamp or other attachment device that holds the pump in a fixed position relative to the support structure. At times, however, it is necessary or desirable to be able to rotate the medical device relative to the support structure. A number of prior art devices have a gooseneck or flexible section that supports the object being held and provides the movement for the object. These support devices do not have a mounting member that protects against dropping the supported device after the member is loosened to attach or replace the supported device. For example, U.S. Pat. No. 5,163,752 to Copeland shows the gooseneck for flexure and the object being held in place with a Velcro® strap. The strap may come loose and the device can dislodge from the support. For example, U.S. Pat. No. 5,664,750 to Cohen attaches the device at C using the support portion 64. The support 64 is threaded into the camera and uses the various apertures 34, 36 ad 38 to orient the camera. The aperture restricts the orientation and the user may drop the mounted camera when moving it from one aperture to the next.

For example, enteral feeding pumps are often somewhat oblong; as such, they may protrude laterally outwardly from an IV pole by an amount that is undesirable. Therefore, it is desirable to be able to rotate the enteral feeding pump between a first position in which it can be read and adjusted by tending hospital staff—i.e., a position in which it protrudes laterally outwardly from the support structure—and a second, "stowed" position in which the device is more generally "tucked in" or aligned with the support structure.

Because medical devices such as enteral feeding pumps can be expensive and/or delicate equipment, and to protect the patient, it is important that the support mechanism be configured to minimize the risk that the device will fall from the support structure when the device is being adjusted.

SUMMARY OF THE INVENTION

In one aspect of the present invention, a medical device support apparatus mounts a medical device to a support structure so as to permit infinite reorientation of the medical device with respect to the support structure. The support apparatus generally comprises a base mounting member configured to releasably mount the medical device support apparatus on the support structure. A medical device mounting member extending from the base mounting member is configured to co-act with a cooperatively configured attachment portion of the medical device whereby the medical device can be attached to the medical device mounting member. A lockdown member associated with the medical device mounting member has a handle and a set-screw portion attached to the handle for movement with the handle. The set-screw portion is adapted to extend into engagement with the attachment portion of the medical device in a first position in which the set screw portion bears against the attachment portion so as to resist relative rotating motion of the medical device and the medical device mounting member, and in a second position in which the set screw portion does not resist relative rotation of the medical device and the medical device mounting member as strongly as in the first position thereby permitting relative rotation of the medical device with respect to the medical device mounting member. The set screw portion is disposed in the second position to block movement of the medical device attachment portion that would detach the medical device from the medical device mounting member.

In another aspect of the present invention, a medical device support system generally comprises a medical device capable of being supported from a support structure The medical device support system includes an attachment portion. A base mounting member is configured to mount on the support structure. A medical device mounting member extending from and supported by the base mounting member is cooperatively configured to co-act with the attachment portion of the medical device whereby the medical device can be attached to the medical device mounting member. A lockdown member has a handle and a set-screw portion attached to the handle for movement with the handle into to a first position in which the set screw portion bears against said one of the attachment portion and the medical device mounting member to resist relative rotating motion of the medical device attachment portion and the medical device mounting member, and to a second position in which the set screw portion does not as strongly resist rotation of the medical device attachment portion relative to the medical device mounting member thereby permitting relative rotation of the medical device with respect to the medical device mounting member. The set screw portion is disposed in the second position to block movement of the attachment portion that would detach the medical device from the medical device mounting member.

The lockdown member and corresponding circumferential channel at the medical device prevents the device from falling off the device mounting member during use. This provides a degree of safety for the device and the patient. For example, a medical device attached to the device mounting member is a pump. The pump delivers medicine via tubing into the patient through a gastrostomy device such as a Kangaroo® button, sold by the assignee of the present application and disclosed at U.S. Pat. No. 6,458,106 to Meier. As shown in FIG. 10 of the Meier patent, the adapter is positioned through the abdominal and stomach wall with tubing 46 connected to a pump or other delivery mechanism. If the pump should disengage from its mounting member, the tubing attached to the pump and to the jejunal adapter may tear the adapter from within the patient's stomach. A pump like shown in FIG. 9 is typically mounted on a pole "P", which exposes the pump to falling to the floor. The present invention helps protect against the accidental release of the medical device from its mounting member.

BRIEF DESCRIPTION OF THE DRAWINGS

Corresponding reference characters indicate corresponding pars throughout the several views of the drawings.

DETAILED DESCRIPTION OF EMBODIMENTS OF THE INVENTION

Figure 1:
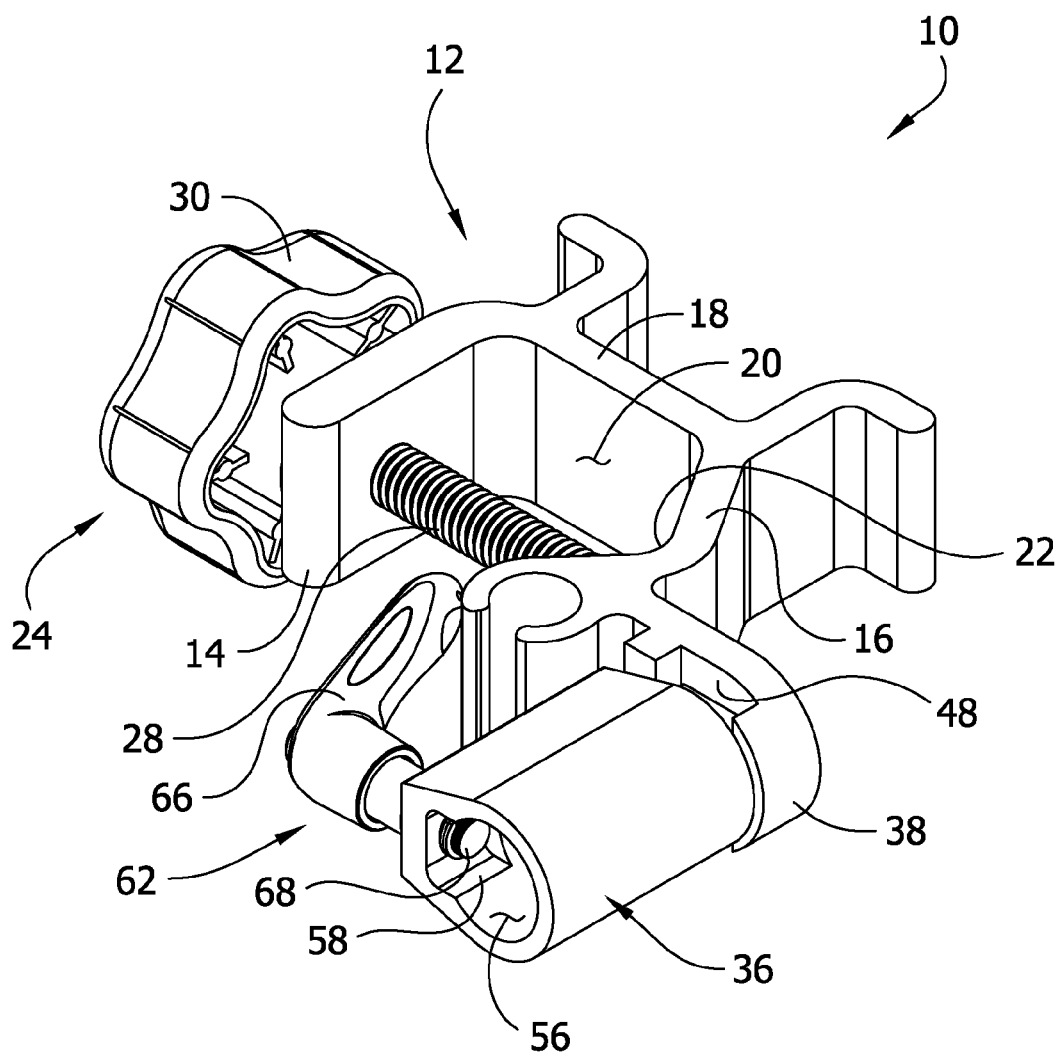
FIG. 1 is a perspective view of a medical device support apparatus.
Figure 2:
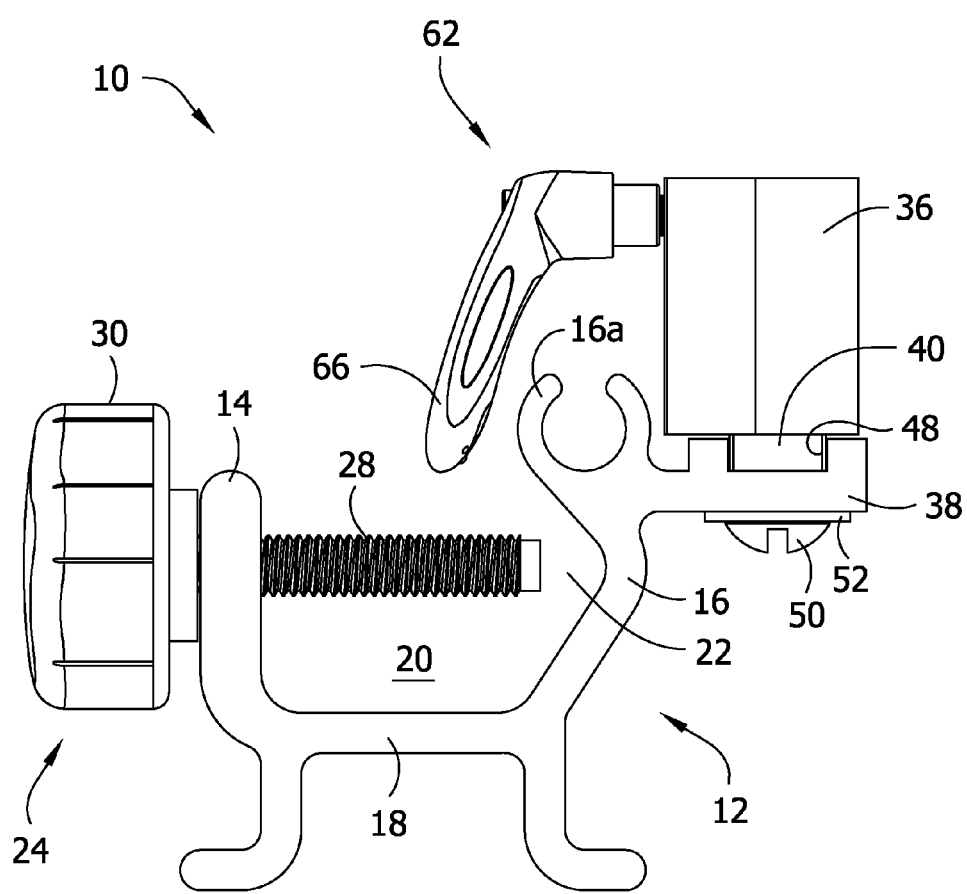
FIG. 2 is a bottom view thereof.
Figure 3:
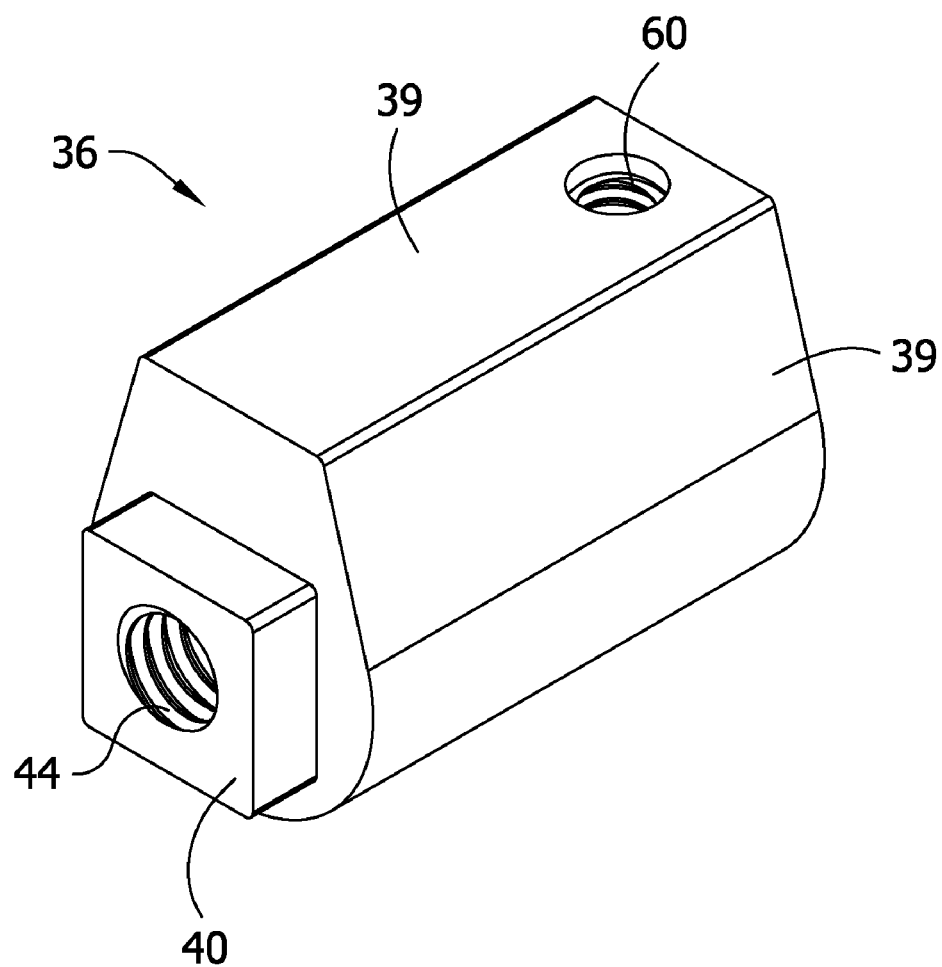
FIG. 3 is a rear perspective view of a medical device mounting member that forms part of the medical device support apparatus shown in FIGS. 1 and 2.
Figure 4:
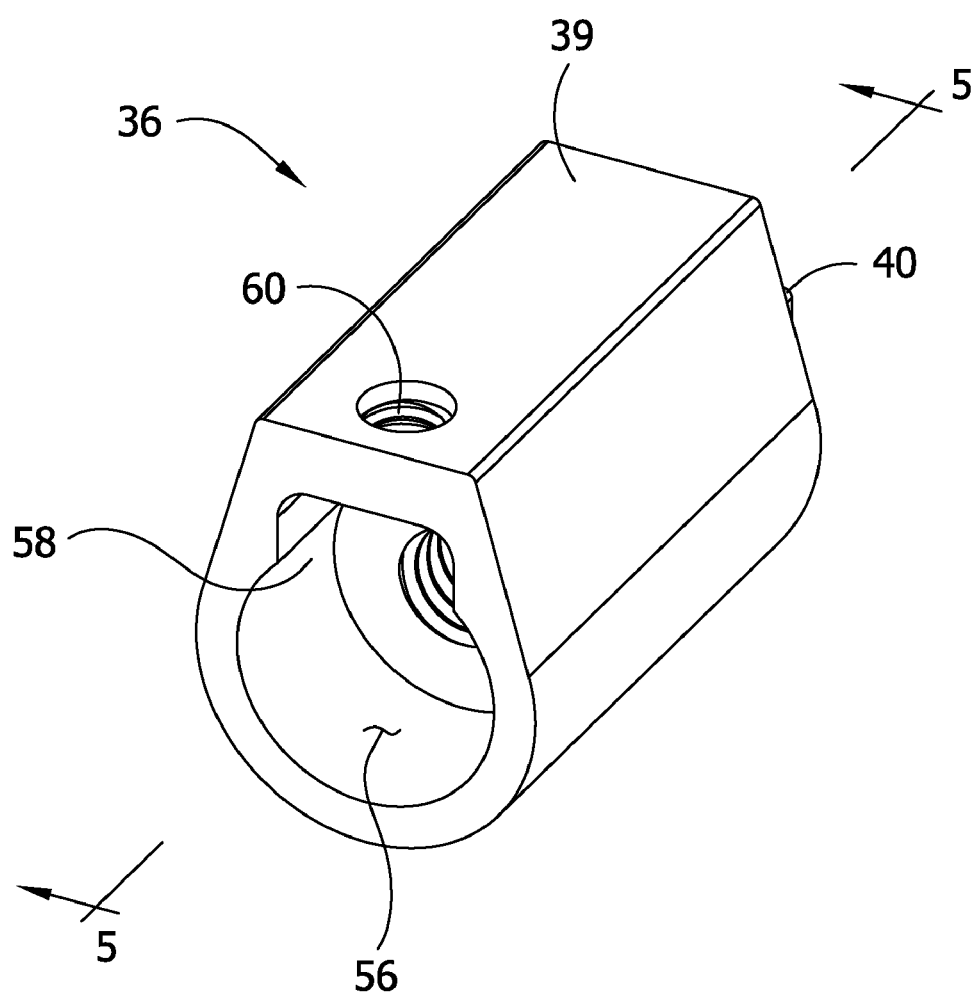
FIG. 4 is a front perspective view of the medical device mounting member.
Figure 5:
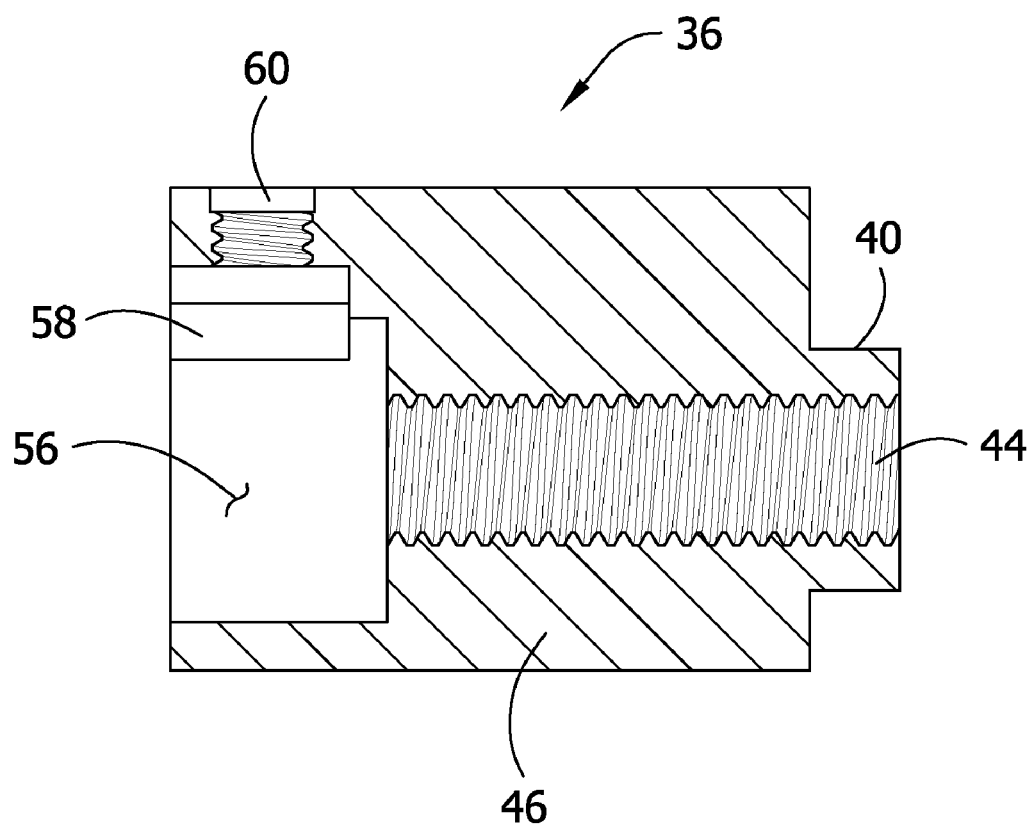
FIG. 5 is a section view of the medical device mounting member shown in FIGS. 3 and 4, taken along the lines 5-5 in FIG. 4.

A medical device support apparatus 10 according to the invention is illustrated in FIGS. 1-10. As illustrated in FIGS. 1 and 2, the support apparatus 10 includes a base mounting member, e.g., a generally C-shaped clamp member 12. It will be understood that other types of mounting members besides a clamp may be used within the scope of the present invention. The clamp member 12 includes first and second arms 14, 16 and back member 18, which together define a channel 20. Second arm 16 is slightly V-shaped so as to define a pole-receiving notch 22.

Figure 9:
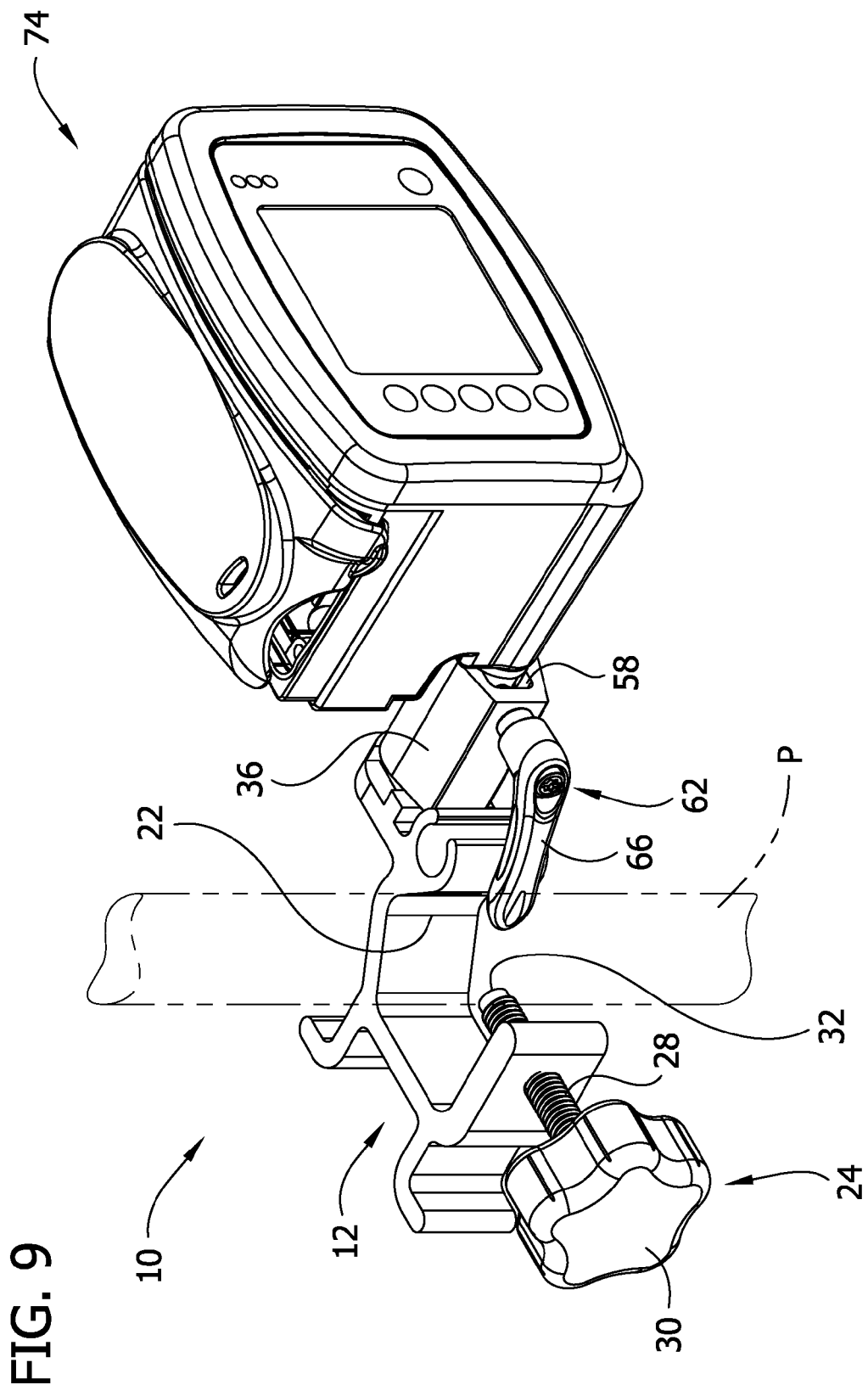
FIG. 9 is a perspective view of the medical device support member of the invention shown in FIGS. 1 and 2 being used to support a medical device, e.g., the medical device shown in FIGS. 7 and 8.
Figure 10:
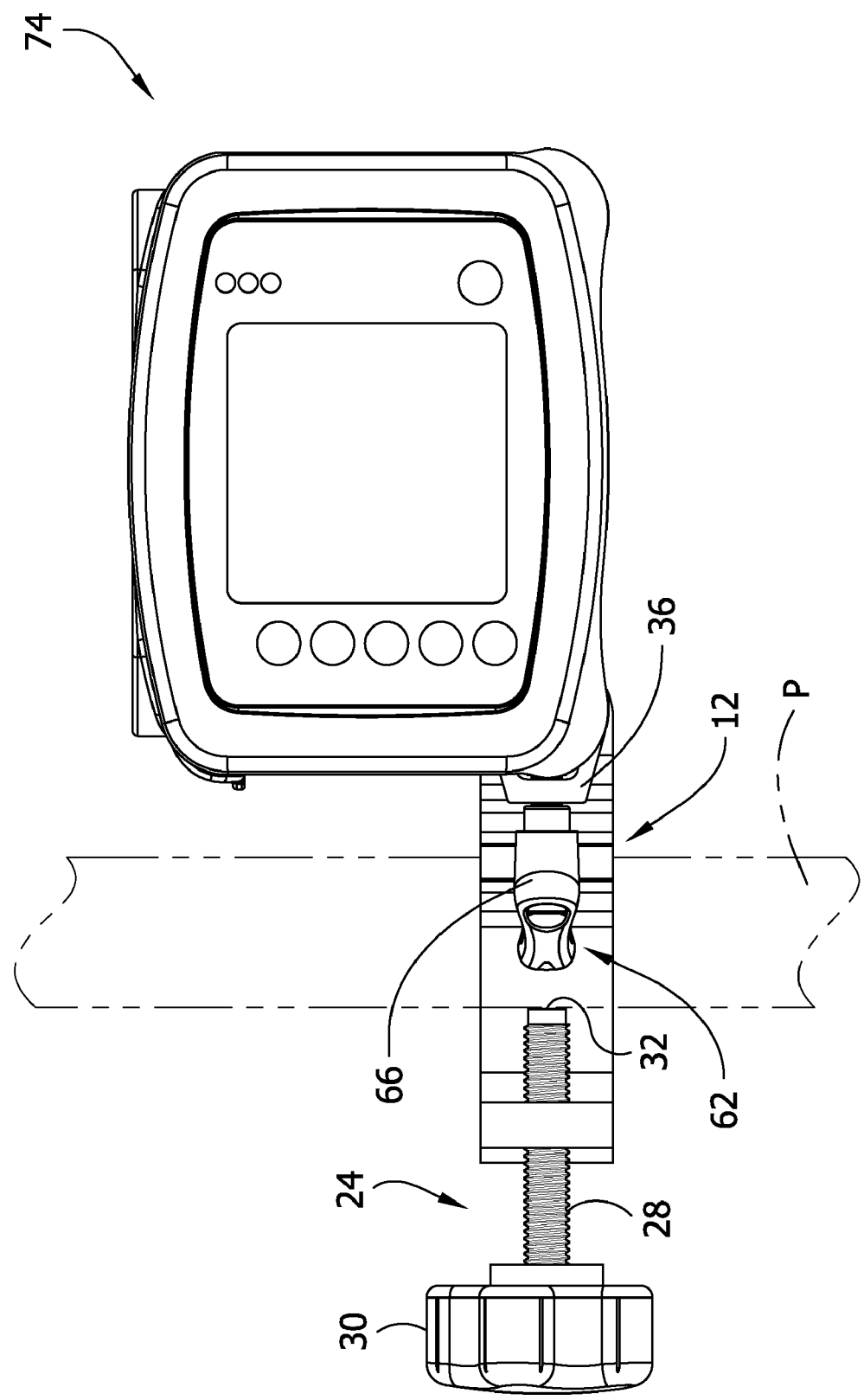
FIG. 10 is a front view of the medical device support member of FIG. 9.

The support apparatus 10 further includes a securing member generally at indicated at 24 by means of which the support apparatus is secured to a support structure, e.g., to an IV pole P (shown in phantom in FIGS. 9 and 10). It will be understood that the support apparatus can be secured to other support structures, such as a bed rail. In particular, the securing member is suitably an externally threaded post 28 with a hand knob 30 attached to a proximal end thereof. The first arm 14 of the clamp member 12 has a threaded hole (not visible) formed through it, generally across from the pole-receiving notch 22 defined by the second arm 16, into which the threaded post 28 screws. Thus, the support apparatus 10 may be secured to the IV pole P as illustrated in FIGS. 9 and 10 by unscrewing the threaded post 28 sufficiently to open up the channel 20; positioning the clamp member 12 around the IV pole, with the support structure received within the pole-receiving notch 22; and screwing the threaded post 28 down against the side of the IV pole, whereby the IV pole is clamped between the distal end 32 of the threaded post and the pole-receiving notch.

At one end of the second arm 14 is a dust cover holder 16a. The holder 16a retains a protective cap (not shown) located over the outlet of an enteral feeding set used with the pump. This allows the practitioner to keep the cap clean and stored in a safe and accessible location for reuse. The L-shaped flanges extending from the back of member 18 are for wrapping the power cord (not shown) of the pump. This allows the practitioner to store the excess cord to prevent it from becoming entangled with the enteral feeding set.

As further illustrated in FIGS. 1 and 2, the medical device support apparatus 10 further includes a medical device mounting member 36 attached to one of the arms of the clamp member 12, i.e., to second arm 16. In particular, a mounting tab 38 extends from the second arm 16, and the medical device mounting member 36 is securely fastened to the mounting tab 38. More particularly, the medical device mounting member 36 is suitably a roughly cylindrical element, with a truncated teardrop cross-section which provides a flat side surface 39. A polygonal key portion 40, suitably square in cross-section, projects from the medical device mounting member 36, at one end thereof, and a threaded hole 44 (FIG. 3) extends through the center of the key portion 40 at least partially into a central body portion 46 of the medical device mounting member 36. A slot 48 is formed in the mounting tab 38. The key portion 40 fits within the slot 48, and the medical device mounting member 36 is secured to the mounting tab 38, i.e., by means of a bolt 50 (and washer 52), the shank of which passes through the hole in the mounting tab 38 and is threaded into the threaded hole 44 in the medical device mounting member 36. It will be appreciated that the polygonal shape of the key portion 40 allows the medical device mounting member 36 to be fastened to the mounting tab 38 in multiple angular orientations (i.e., different angular positions about the longitudinal centerline of the threaded hole 44), but that the key portion 40 prevents the medical device mounting member 36 from rotating relative to the mounting tab 38 once the medical device mounting member is secured to it.

A socket (i.e., a cavity) 56 formed in the medical device mounting member 36 opens at an end of the mounting member 36 opposite the mounting tab 38. Referring now also to FIGS. 3-6, a cutout 58 is formed in the sidewall of the socket 56 at a circumferential position that is closest to the flat side surface 39 of the medical device mounting member 36, and a threaded hole 60 extends from the flat side surface 39 to the cutout 58.

Figure 6:
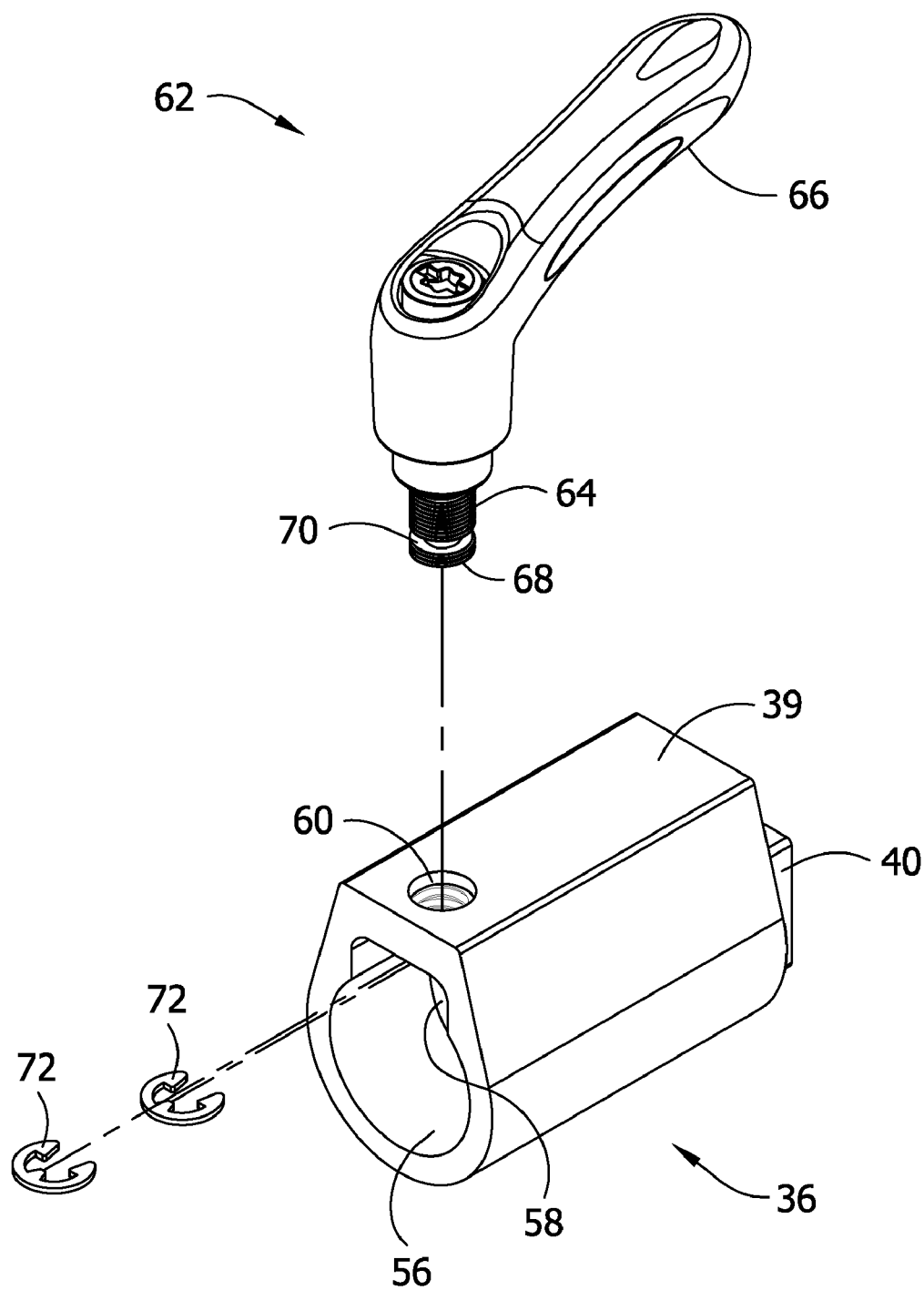
FIG. 6 is a perspective view of the medical device mounting member shown in FIGS. 3-5, along with a lockdown member used in conjunction with it.

As best illustrated in FIG. 6, the medical device support apparatus 10 further includes a lockdown member 62 that can be used to fix the position of a supported medical device. In particular, the lockdown member 62 suitably includes a set-screw portion 64 which screws down into the threaded hole 60 and a handle 66 provided to facilitate turning and threading of the set-screw portion into the threaded hole The threaded shank of the set-screw portion 64 is long enough that the distal end 68 of the set-screw portion will extend all the way through the cutout 58 and into the socket 56 of the medical device mounting member 36 when the lockdown member 62 is tightened, for the purpose which will be explained more fully below. Suitably, a circumferential channel 70 is formed near the distal end 68 of the set-screw portion 64, which circumferential channel is an area devoid of threads and which may extend slightly radially into the shank of the set-screw portion. After the set-screw portion 64 has been screwed down into the threaded hole 60 such that the distal end 68 protrudes into the socket 56, one or more C-clips 72 (two are illustrated) may be clipped onto the set-screw portion 64 by being inserted into the circumferential channel 70. The C-clips 72 prevent the lockdown member 62 from being unscrewed all the way from the medical device mounting member 36 once they have been installed, thus preventing the pump from becoming dislodged from the medical device mounting member. This is an important safety issue, as described above, when the pump from improper tightening or becoming loose during use (i.e. vibration), falls off prior art structure. The C-clips reside within the cutout 58 (for which purpose the cutout 58 is provided in the medical device mounting member 36). The set-screw portion 64 can be secured against withdrawal from the socket.

Figure 7:
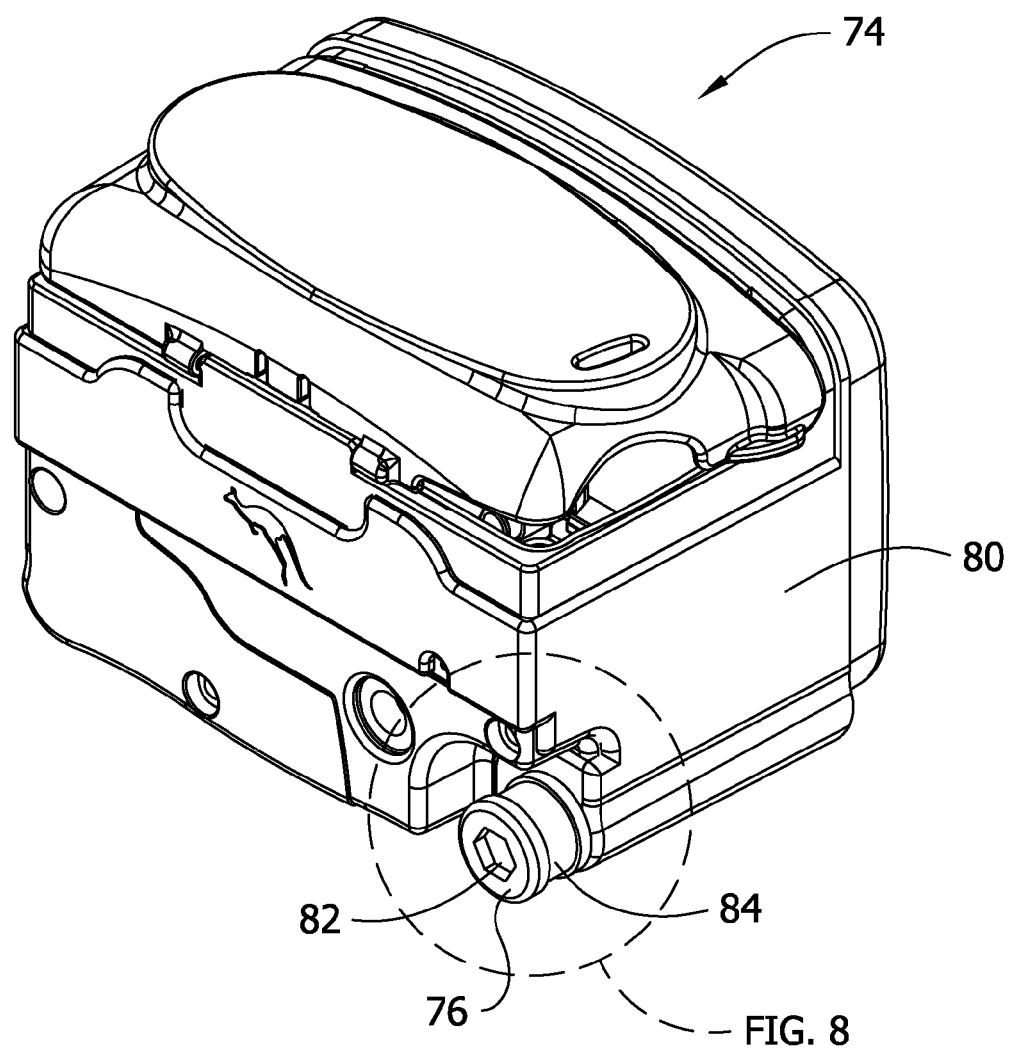
FIG. 7 is a rear perspective view of an enteral feeding pump that can be supported by the medical device support apparatus of the invention shown in FIGS. 1 and 2.
Figure 8:
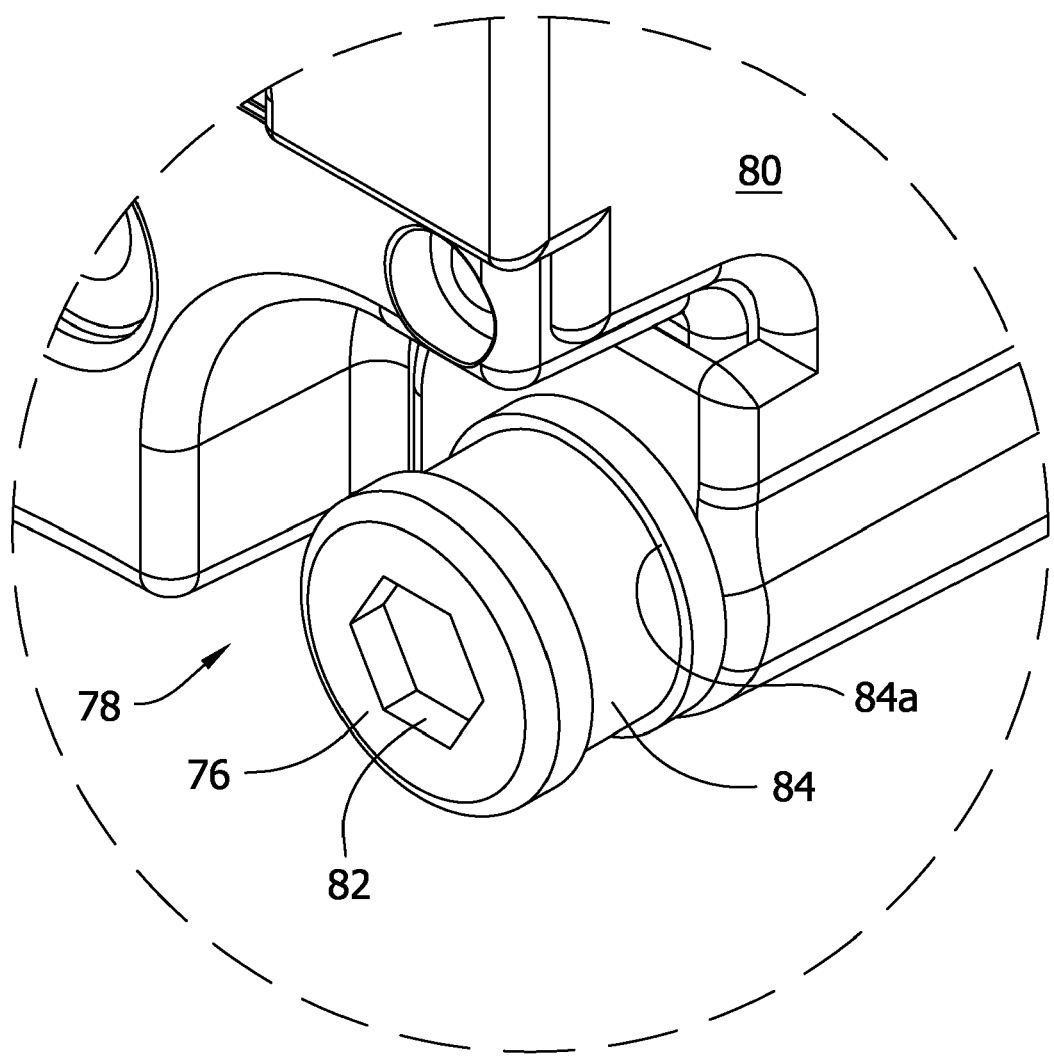
FIG. 8 is an enlarged view of the circled portion shown in FIG. 7.

As illustrated in FIGS. 7 and 8, a medical device in the form of an enteral feeding pump 74, includes a post indicated generally at 76, which suitably resides within a recessed corner portion 78 of the housing 80 of the enteral feeding pump. The post 76 suitably includes a threaded shank (not illustrated) that screws into a threaded hole (not illustrated) formed in the housing 80, and a hexagonal recess 82 is provided in the end face of the post 76 to facilitate screwing the post 76 into the threaded hole, e.g., using on Allen wrench. Furthermore, the post 76 includes a circumferential channel 84.

As illustrated in FIGS. 9 and 10, the feeding pump 74 is attached to the support apparatus 10 by inserting the post 76 into the socket 56 formed in the medical device mounting member 36. The post 76 bottoms out in the socket 56 so that the circumferential channel 84 of the post is aligned to receive the distal end 68 of the set-screw portion 64. The lockdown member 62 is turned until the distal end 68 of the set-screw portion 64 bears against the floor of the channel 84. The set-screw portion 64 prevents the post 76 and hence that pump 74 from rotating relative to the mounting member 36 and support apparatus 10. Preferably, less that a full turn of the handle 66 is required to lock the pump 74 in a selected position. More preferably, locking is achieved with a turn of the handle 66 of about 90°. The feeding pump 74 can be quickly and easily moved from one position (e.g., the straight-out, horizontal position shown in FIGS. 9 and 10 for reading and/or adjusting the feeding pump) to another position (e.g., a "flipped-up," vertically oriented stowed position, not shown) by slightly loosening the lockdown member 62, e.g., by turning the handle 66 about ⅛ to ¼ of a turn; rotating the pump to a selected orientation 74; then retightening the lockdown member 62. It will be appreciated that the pump 74 can be rotated to any desired position with respect to the support apparatus 10 because the channel 84 extends continuously about the circumference of the post 76. The distal end 68 of the set-screw portion 64 remains extended into the circumferential channel 84 around the post member 76; but no longer bears against the post in the channel. The location of the distal end 68 in the channel 84 prevents the post 76 from being removed completely from the medical device mounting member 36, thus reducing the risk that the pump 74 will be dropped and damaged. However, repositioning of the pump 74 can be quickly and easily carried out by turning the handle 66 to loosen or terminate the engagement of the set-screw portion 64 with the post 76. This rapid positioning is because a distance between the clips 72 and distal end of the set screw 68 is preset by the placement of the clips 72 along the set screw 64. This distance is adjusted to maintain a sufficient portion of the set screw 64 within the channel 84 such that the distal end 68 does not raised above the channel wall 84a when the practitioner loosens the lockdown member 62 for repositioning the supported medical device. Also, the required amount of turn is minimized allowing the practitioner to work more efficiently. The positioning of the clips 72 from the distal end 68 limits the travel of the lockdown member 62 thereby reducing the time to loosen and tighten the support medical device.

In another embodiment (not illustrated), the medical device mounting member could have a post with a circumferential channel instead of a socket, and the medical device could have a socket instead of a post. The lockdown member would then screw into the side of the medical device and protrude into the socket formed therein to secure the medical device to the mounting member. In other words, such an embodiment would represent a simple transposition of the operative elements of the mounting member and the medical device and is also deemed to be within the scope of the invention.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above construction without departing from the scope of the invention, it is intended that all matter contained in the above description or shown in the accompanying drawings shall be interpreted as illustrative and not in a limiting sense. It is understood that any of the particular embodiments of the present invention may include one or more of the aspects or features of the invention as described herein and illustrated in the drawings.

What is claimed is:

1. A medical device support apparatus for mounting a medical device to a support structure so as to permit infinite reorientation of the medical device with respect to the support structure, the support apparatus comprising:
    a base mounting member configured to releasably mount the medical device support apparatus on the support structure;
    a medical device mounting member extending from the base mounting member, said medical device mounting member having a socket sized and shaped for receiving a cooperatively configured attachment portion of the medical device, a recess extending into an inner surface of the socket, and a threaded hole extending through the medical device mounting member and opening into the recess, said attachment portion having a smaller width portion and a larger width portion; and
    a lockdown member associated with the medical device mounting member, the lockdown member having a handle and a set-screw portion attached to the handle and threadably received in the threaded hole in the medical device mounting member for movement with the handle and adapted to extend into engagement with the attachment portion of the medical device in a first position in which the set screw portion bears against the attachment portion so as to resist relative rotating motion of the medical device and the medical device mounting member, and in a second position in which the set screw portion extends into the socket so the set screw portion is aligned with the smaller width portion and does not resist relative rotation of the medical device and the medical device mounting member as strongly as in the first position thereby permitting infinite rotation of the medical device with respect to the medical device mounting member, the set screw portion being disposed in the second position to prevent the larger width portion of the medical device mounting member from passing the set screw portion extending into the socket to prevent the attachment portion of the medical device withdrawing from the socket of the medical device mounting member.

2. A medical device support apparatus as set forth in claim 1 wherein the set screw portion is adapted to be secured in the threaded hole by a clip attached to the set screw portion and received in the recess.

3. A medical device support apparatus as set forth in claim 2 wherein the set screw portion has an annular channel formed therein for receiving the clip.

4. A medical device support apparatus as set forth in claim 2, wherein a preset distance between the clip and a distal end of the set screw portion prevents the distal end of the set screw portion from being withdrawn from the socket to prevent the medical device from detaching from the medical device mounting member.

5. A medical device support apparatus as set forth in claim 1 wherein the set screw portion has an axis of rotation, the handle further comprises an elongate handle extending radially and axially away from the set screw portion for grasping to rotate the set screw portion.

6. A medical device support apparatus as set forth in claim 1 wherein said base mounting member comprises a generally C-shaped clamp member having first and second arms and a back member defining a channel; the first arm having a threaded hole therein, a threaded post extending through the threaded hole, the second arm being slightly V-shaped so as to define a pole-receiving notch across from said threaded hole, whereby said medical device support apparatus can be clamped to the support structure.

7. A medical device support apparatus as set forth in claim 6 further comprising a hand knob at a proximal end of said threaded post.

8. A medical device support apparatus as set forth in claim 1, further comprising a mounting tab extending from the base mounting member, wherein the medical device mounting member is releasably connected to the mounting tab.

9. A medical device support apparatus as set forth in claim 1, wherein the set screw portion is retained by the medical device mounting member against withdrawal of a distal end of the set screw portion from the socket.

10. A medical device support apparatus as set forth in claim 1 in combination with a medical device having an attachment portion comprising a medical device attachment post attachable to the medical device and adapted for insertion into the socket of the medical device mounting member to secure the medical device to the medical device mounting member, the post including a circumferential channel that receives the set screw portion of the lockdown member in both the first and second positions of the lockdown member.

11. A medical device support apparatus for mounting a medical device to a support structure so as to permit infinite reorientation of the medical device with respect to the support structure, the support apparatus comprising:
a base mounting member configured to releasably mount the medical device support apparatus on the support structure;
a medical device mounting member extending from the base mounting member, said medical device mounting member being configured to co-act with a cooperatively configured attachment portion of the medical device whereby the medical device can be attached to the medical device mounting member; and
a lockdown member associated with the medical device mounting member, the lockdown member having a handle, a set-screw portion attached to the handle and a clip mounted on the set screw portion for conjoint axial movement with the set screw portion, the set screw portion adapted to extend into engagement with the attachment portion of the medical device in a first position in which the set screw portion bears against the attachment portion so as to resist relative rotating motion of the medical device and the medical device mounting member, and in a second position in which the set screw portion does not resist relative rotation of the medical device and the medical device mounting member as strongly as in the first position thereby permitting infinite rotation of the medical device with respect to the medical device mounting member, the set screw portion being disposed in the second position to prevent movement of the medical device attachment portion that would detach the medical device from the medical device mounting member, wherein the set screw portion has a circumferentially extending channel formed therein, the clip being received in the channel.

\* \* \* \* \*